United States Patent [19]

Fujii et al.

[11] Patent Number: 4,481,203

[45] Date of Patent: Nov. 6, 1984

[54] COMPOSITION CONTAINING 1-(N-HEXYLCARBAMOYL)-5-FLUOROURACIL AND URACIL

[75] Inventors: Setsuro Fujii, Toyonaka; Norio Unemi; Setsuo Takeda, both of Tokushima, all of Japan

[73] Assignee: Taiho Pharmaceutical Company, Limited, Tokyo, Japan

[21] Appl. No.: 212,543

[22] Filed: Dec. 3, 1980

Related U.S. Application Data

[60] Division of Ser. No. 15,161, Feb. 13, 1979, Pat. No. 4,328,229, which is a continuation-in-part of Ser. No. 891,343, Mar. 29, 1978, abandoned.

[30] Foreign Application Priority Data

Apr. 5, 1977 [JP] Japan .................................. 52-39341
Feb. 10, 1978 [JP] Japan .................................. 53-14676

[51] Int. Cl.³ ............................................ A61K 31/505
[52] U.S. Cl. .................................................... 424/251
[58] Field of Search ......................................... 424/251

[56] References Cited

PUBLICATIONS

Burchenal et al., Cancer Chemotherapy Repts., 6, pp. 1-5 (1960).
Chemical Abstracts 86: 50590p (1976).
Jato et al., J. of Pharm. Sciences, 62, pp. 1975-1978 (Dec. 1978).
Jato et al., J. of Pharm. Sciences, 64, pp. 943-946 (Jun. 1975).

Primary Examiner—Jerome D. Goldberg
Attorney, Agent, or Firm—Murray, Whisenhunt and Ferguson

[57] ABSTRACT

A composition for delivering 5-fluorouracil to cancer tissues, of a cancer sensitive to 5-fluorouracil, in warm blooded animals, comprising effective amounts of 1-(n-hexylcarbamoyl)-5-fluorouracil and uracil in a molar ratio of 1:0.1-10, respectively.

8 Claims, No Drawings

COMPOSITION CONTAINING 1-(N-HEXYLCARBAMOYL)-5-FLUOROURACIL AND URACIL

This is a divisional application of Ser. No. 15,161, filed Feb. 13, 1979, now U.S. Pat. No. 4,328,299, which is a continuation-in-part of Ser. No. 891,343, filed Mar. 29, 1978, now abandoned.

This invention relates to anti-cancer compositions, for delivering 5-fluorouracil to cancer tissues, of a cancer sensitive to 5-fluorouracil, in warm blooded animals.

In recent years, various excellent anti-cancer compositions have been introduced into use for the chemotherapy of malignant cancers with progressively improved results. Chemotherapeutic effects so far achieved nevertheless still remain temporary and are not always satisfactory in completely inhibiting the proliferation of cancerous tissues and enabling patients to survive a long period of time. The anti-cancer compositions frequently used for clinical purposes at present are predominantly those consisting essentially of a 5-fluorouracil, and various 5-fluorouracils will be developed in the future. However, anti-cancer compositions comprising a compound having a 5-fluorouracil as its skeleton and serving as the active component thereof have both merits and demerits. For example, 5-fluorouracil, although highly effective, has high toxicity and marked side effects.

The object of this invention is to provide anti-cancer compositions for delivering 5-fluorouracil to cancer tissues, of a cancer sensitive to 5-fluorouracil, in warm blooded animals, or with the composition having a high anti-cancer effect but suppressed toxicity and side effects, said composition comprising a pharmaceutically effective amount of at least one 5-fluorouracil (a) and an effective amount of uracil (b), the 5-fluorouracil (a) being 1-(n-hexyl-carbamoyl)-5-fluorouracil.

Although uracil (b) itself has no anti-cancer effect whatever, the use of the 5-fluorouracil (a) in combination therewith according to this invention produces a greatly enhanced anti-cancer effect, resulting in a therapeutic index of about 1.6 to 4.1 times that of the 5-fluorouracil alone. With the anti-cancer composition of this invention administered, cancer tissues have an exceedingly increased 5-fluorouracil concentration, whereas the other tissues, such as the blood serum, will exhibit little or no increase in the concentration of 5-fluorouracil. This shows that the present composition is an ideal therapeutic agent for cancers, by delivering 5-fluorouracil to cancer tissues, of a cancer sensitive to 5-fluorouracil, in warm-blooded animals.

The compound 1-(n-hexyl-carbamoyl)-5-fluorouracil is disclosed in Japanese published unexamined patent application No. 148365/1975.

When the 5-fluorouracil (a) is administered in combination with uracil (b) according to this invention, the 5-fluorouracil (a) is converted into 5-fluorouracil and consequently the 5-fluorouracil concentration remarkably increases in cancer tissues.

The amount of uracil (b) to be used relative to the 5-fluorouracil (a) for the preparation of the compositions according to this invention is dependent on the kind of the 5-fluorouracil used. Generally about 0.02 to about 10 mols, preferably about 0.05 to 5 mols, more preferably about 0.1 to 2 mols, of uracil (b) is used per mol of the 5-fluorouracil (a).

The anti-cancer compositions of this invention are useful for the treatment of cancers in warm-blooded animals, wherein the cancer is a cancer sensitive to 5-fluorouracil.

According to this invention, the 5-fluorouracil (a) and uracil (b) can be administered to warm-blooded animals individually in separate doses but are given preferably at the same time in the form of a single preparation. The compositions of this invention can be administered in the desired form of preparation in accordance with the therapy contemplated. They are provided for example as tablets, capsules and granules for oral administration or as parenteral solutions and suppositories for non-oral administration. These preparations can be formulated with use of carriers already known in the art.

Examples of useful carriers for making oral preparations are lactose, sucrose, starch, talc, magnesium stearate, crystalline cellulose, methyl cellulose, hydroxypropyl cellulose, hydroxypropylmethyl cellulose, carboxymethyl cellulose, glycerin, sodium alginate, gum arabic, etc. The amount of the 5-fluorouracil (a) in oral preparations may preferably be 10 to 200 mg per dosage unit. Carriers suitable for parenteral preparations are, for example, water, physiological saline solution, etc. which can be used with tris(hydroxymethyl)aminomethane, soduim carbonate, sodium hydroxide or the like serving as a solubilizer or pH adjusting agent. The parenteral preparations contain preferably 50 to 1000 mg of the 5-fluorouracil (a) per dosage unit. Suitable carriers for preparing suppositories are for example cacao butter, Witepsol-W35 (fat, trade mark of Dynamit Nobel A.G. of Germany). The suppositories may contain preferably 250 to 1000 mg of the 5-fluorouracil (a) per piece.

The results of biological applications and basic efficacy tests show that the preferred dose of the present compositions, although dependent on the kind of 5-fluorouracil, is usually about 0.5 to about 150 mg/kg, preferably about 0.5 to about 50 mg/kg calculated as the quantity of 5-fluorouracil. These values are in terms of the quantity per kilogram of the body weight of the warm-blooded animal per day.

Also provided are examples of anti-cancer compositions of nonelected inventions, presented for the purpose of illustrating other types of pharmaceutical formulations, and providing comparative pharmacology. In these examples and tables, the listed compounds can be identified as follows:

5-Fluorouracil (Compound 1)
1-(2-Tetrahydrofuryl)-5-fluorouracil (Compound 2)
1,3-bis(2-Tetrahydrofuryl)-5-fluorouracil (Compound 3)
1-(n-Hexylcarbamoyl)-5-fluorouracil (Compound 4)
1-Ethoxymethyl-5-fluorouracil (Compound 5)
2-(n-Butyl)-5-fluorouracil (Compound 6)
3-(2-Tetrahydrofuryl)-5-fluorouracil (Compound 7)
1-Benzenesulfonyl-5-fluorouracil (Compound 8)
1-Ethoxycarbonyl-5-fluorouracil (Compound 9)
1-(n-Butyryl)-5-fluorouracil (Compound 10)
1-(n-Butyl)-5-fluorouracil (Compound 11)
2,4-Dibenzyl-5-fluorouracil (Compound 12)
1-(3-Chlorotetrahydropyran-2-yl)-5-fluorouracil (Compound 13)
1-Tetrahydrofurfuryl-5-fluorouracil (Compound 14)
1-(p-Toluenesulfonyl)-5-fluorouracil (Compound 15)
1-(2-Cyanoethyl)-5-fluorouracil (Compound 16)
3-Benzoyl-5-fluorouracil (Compound 17)

1-(2-Tetrahydrofuryl)-3-benzoyl-5-fluorouracil (Compound 18)
1-(2-Tetrahydrofuryl)-3-methylthiomethyl-5-fluorouracil (Compound 19)
1-(2-Tetrahydrofuryl)-3-(n-decyl)-5-fluorouracil (Compound 20)
2-(sec-Butyl)-5-fluorouracil (Compound 21)
2-Phenyl-5-fluorouracil (Compound 22)
2-Ethyl-5-fluorouracil (Compound 23)
2-Tetrahydrofurfuryl-5-fluorouracil (Compound 24)
2-Cetyl-5-fluorouracil (Compound 25)
2-(n-Decyl)-5-fluorouracil (Compound 26)
2-(n-Hexyl)-5-fluorouracil (Compound 27)
2,4-di(tert-Butyl)-5-fluorouracil (Compound 28)
2,4-Diphenyl-5-fluorouracil (Compound 29)
1-Methyl-5-fluorouracil (Compound 30)
1-(2-Tetrahydrofuryl)-3-methyl-5-fluorouracil (Compound 31)
1-Benzoyl-5-fluorouracil (Compound 32)
1-Isobutoxycarbonyl-5-fluorouracil (Compound 33)
1,3-bis(Isobutoxycarbonyl)-5-fluorouracil (Compound 34)
1,3-bis(Ethoxymethyl)-5-fluorouracil (Compound 35)
1-(2-Tetrahydropyranyl)-5-fluorouracil (Compound 36)
1,3-bis(2-Tetrahydropyranyl)-5-fluorouracil (Compound 37)
1,3-bis(Tetrahydrofurfuryl)-5-fluorouracil (Compound 38)
1,3-bis(2-Cyanoethyl)-5-fluorouracil (Compound 39)
1-(n-Butylcarbamoyl)-5-fluorouracil (Compound 40)
4-n-Butyl-5-fluorouracil (Compound 41)
2,4-di(n-Butyl)-5-fluorouracil (Compound 42)
2,4-Ditetrahydrofurfuryl-5-fluorouracil (Compound 43)

Given below are examples of anti-cancer compositions prepared according to this invention.

| Preparation 1 | |
|---|---|
| Compound 2 | 200 mg |
| Uracil | 40 mg |
| Lactose | 100 mg |
| Crystalline cellulose | 57 mg |
| Magnesium stearate | 3 mg |
| | 400 mg (per capsule) |

An encapsulated preparation is formulated from the above ingredients.

| Preparation 2 | |
|---|---|
| Compound 3 | 100 mg |
| Uracil | 50 mg |
| Lactose | 33 mg |
| Crystalline cellulose | 15 mg |
| Magnesium stearate | 2 mg |
| Talc | 3 mg |
| Corn starch | 14 mg |
| Hydroxypropylmethyl cellulose | 10 mg |
| | 227 mg (per tablet) |

A tableted preparation is formulated from the above ingredients.

| Preparation 3 | |
|---|---|
| Compound 4 | 100 mg |
| Uracil | 50 mg |
| Lactose | 340 mg |
| Corn starch | 500 mg |
| Hydroxypropylmethyl cellulose | 10 mg |
| | 1,000 mg (per pack) |

A granular preparation is formulated from the above ingredients.

| Preparation 4 | |
|---|---|
| Compound 3 | 50 mg |
| Uracil | 50 mg |
| Lactose | 390 mg |
| Corn starch | 500 mg |
| Hydroxypropyl cellulose | 10 mg |
| | 1,000 mg (per pack) |

A granular preparation is formulated from the above ingredients.

| Preparation 5 | |
|---|---|
| Compound 5 | 200 mg |
| Uracil | 50 mg |
| Lactose | 97 mg |
| Crystalline cellulose | 50 mg |
| Magnesium stearate | 3 mg |
| | 400 mg (per capsule) |

An encapsulated preparation is formulated from the above ingredients.

| Preparation 6 | |
|---|---|
| Compound 1 | 250 mg |
| Uracil | 50 mg |
| Tris(hydroxymethyl)-aminomethane | 290 mg |
| Distilled water | (suitable amount) |
| | 5 ml (per ampule) |

A parenteral solution is prepared from the above ingredients.

| Preparation 7 | |
|---|---|
| Compound 2 | 400 mg |
| Uracil | 40 mg |
| Sodium carbonate | 560 mg |
| Sodium hydroxide | 80 mg |
| Distilled water | (suitable amount) |
| | 10 ml (per ampule) |

A parenteral solution is prepared from the above ingredients.

| Preparation 8 | |
|---|---|
| Compound 2 | 1,000 mg |
| Uracil | 200 mg |
| Witepsol W-35 | 1,000 mg |
| | 2,200 mg (per piece) |

Suppositories are prepared from the above ingredients.

| Preparation 9 | |
|---|---|
| Compound 2 | 50 mg |
| Uracil | 200 mg |
| Lactose | 340 mg |
| Corn starch | 400 mg |
| Hydroxypropyl cellulose | 10 mg |
| | 1,000 mg (per pack) |

A granular preparation is formulated from the above ingredients.

| Preparation 10 | |
|---|---|
| Compound 3 | 50 mg |
| Uracil | 200 mg |
| Lactose | 90 mg |
| Crystalline cellulose | 57 mg |
| Magnesium stearate | 3 mg |
| | 400 mg (per capsule) |

An encapsulated preparation is formulated from the above ingredients.

| Preparation 11 | |
|---|---|
| Compound 3 | 50 mg |
| Uracil | 100 mg |
| Lactose | 33 mg |
| Crystalline cellulose | 15 mg |
| Magnesium stearate | 2 mg |
| Talc | 3 mg |
| Corn starch | 14 mg |
| Hydroxypropylmethyl cellulose | 10 mg |
| | 227 mg (per tablet) |

A tableted preparation is formulated from the above ingredients.

| Preparation 12 | |
|---|---|
| Compound 4 | 50 mg |
| Uracil | 200 mg |
| Lactose | 97 mg |
| Crystalline cellulose | 50 mg |
| Magnesium stearate | 3 mg |
| | 400 mg (per capsule) |

An encapsulated preparation is formulated from the above ingredients.

| Preparation 13 | |
|---|---|
| Compound 5 | 50 mg |
| Uracil | 100 mg |
| Lactose | 340 mg |
| Corn starch | 500 mg |
| Hydroxypropylmethyl cellulose | 10 mg |
| | 1,000 mg (per pack) |

A granular preparation is formulated from the above ingredients.

| Preparation 14 | |
|---|---|
| Compound 1 | 100 mg |
| Uracil | 250 mg |
| Tris(hydroxymethyl)-aminomethane | 400 mg |
| Distilled water | (suitable amount) |
| | 5 ml (per ampule) |

A parenteral solution is prepared from the above ingredients.

| Preparation 15 | |
|---|---|
| Compound 2 | 100 mg |
| Uracil | 150 mg |
| Sodium carbonate | 440 mg |
| Sodium hydroxide | 60 mg |
| Distilled water | (suitable amount) |
| | 10 ml (per ampule) |

A parenteral solution is prepared from the above ingredients.

| Preparation 16 | |
|---|---|
| Compound 3 | 500 mg |
| Uracil | 500 mg |
| Witepsol W-35 | 1,000 mg |
| | 2,000 mg (per piece) |

Suppositories are prepared from the above ingredients.

Compositions of this invention are tested in cancer-bearing rats to determine the concentrations of 5-fluorouracil in the blood as well as in cancer tissues and to determine anti-cancer effects.

(1) Determination of concentrations of 5-fluorouracil in the blood and cancer tissues Ascites cells ($5 \times 10^6$) of AH-130 are subcutaneously transplanted in the armpit portion of male rats of Donryu strain weighing about 200 g. Seven days thereafter, the rats with cancer cells weighing at least 2 g are used, five rats in each group.

An composition comprising a 5-fluorouracil (a) alone or in combination with uracil (b) in the proportion(s) listed in Table 1 is suspended in a 5% solution of gum arabic immediately before use, and the suspension is orally given to the animal at the listed dose. Two, four and eight hours after the administration, the blood serum and cancer tissue homogenate are collected, each of which is acidified with hydrochloric acid and extracted with chloroform. The resulting aqueous layer is examined for antibiotic activity according to the thin-cup method (Media Circle, Vol. 92, p. 259, 1967) with use of *Staphylococcus aureus* 209P strain. The results are give in Table 1 in terms of 5-fluorouracil concentration.

TABLE 1

| 5-Fluorouracil (a) | Uracil (b) | Concentration of 5-fluorouracil (µg/ml) | | | | | |
|---|---|---|---|---|---|---|---|
| | | In blood | | | In cancer tissues | | |
| Compd. No. | (m·mol/kg) | (m·mol/kg) | 2 hr | 4 hr | 8 hr | 2 hr | 4 hr | 8 hr |
| 1 | 0.08 | None | 0.11 | 0.02 | — | 0.34 | 0.16 | 0.05 |
| | | 0.08 | 0.55 | 0.03 | — | 0.72 | 0.43 | 0.18 |
| 2 | 0.5 | None | 0.09 | 0.07 | 0.04 | 0.12 | 0.16 | 0.09 |
| | | 0.5 | 0.86 | 0.07 | 0.05 | 1.45 | 0.94 | 0.38 |
| | | 0.1 | 0.08 | 0.06 | 0.05 | 0.18 | 0.30 | 0.22 |
| 3 | 0.5 | None | 0.45 | 0.35 | 0.11 | 0.60 | 0.80 | 0.20 |

TABLE 1-continued

| 5-Fluorouracil (a) | | Uracil (b) | Concentration of 5-fluorouracil (μg/ml) | | | | | |
|---|---|---|---|---|---|---|---|---|
| | | | In blood | | | In cancer tissues | | |
| Compd. No. | (m·mol/kg) | (m·mol/kg) | 2 hr | 4 hr | 8 hr | 2 hr | 4 hr | 8 hr |
| | | 0.5 | 1.95 | 0.42 | 0.11 | 3.15 | 3.88 | 1.12 |
| 4 | 0.5 | None | 3.20 | 1.31 | 0.41 | 0.90 | 0.63 | 0.13 |
| | | 0.5 | 7.40 | 1.25 | 0.50 | 2.50 | 1.83 | 0.55 |
| 5 | 0.5 | None | 0.04 | 0.02 | — | 0.05 | 0.06 | — |
| | | 0.5 | 0.15 | 0.03 | — | 0.55 | 0.75 | 0.38 |

(2) Determination of effects

Ascites cells ($5 \times 10^6$) of AH-130, are subcutaneously transplanted in the armpit of male Donryu rats weighing about 200 g (ten rats in each group). An composition comprising a 5-fluorouracil (a) alone or in combination with uracil (b) in the proportion(s) listed in Table 2 is suspended in a 5% solution of gum arabic immediately before use. Twenty-four hours after the transplantation and during the following seven consecutive days the suspension is orally given to the animal once every day at the dose listed in Table 2. On the 10th day after the transplantation, the tumor is removed from the body and weighed to calculate the average weight (T) of the tumors in the group to which the composition has been given and the corresponding weight (C) in the control group to determine the ratio T/C. The results are listed in Table 2.

TABLE 2

| 5-Fluorouracil (a) | | Uracil (b) | Anti-cancer effect |
|---|---|---|---|
| Compd. No. | (m.mol/kg) | (m.mol/kg) | (T/C) |
| 1 | 0.08 | None | 0.69 |
| | | 0.16 | 0.32 |
| | | 0.08 | 0.59 |
| 2 | 0.5 | None | 0.65 |
| | | 1 | 0.06 |
| | | 0.5 | 0.17 |
| | | 0.2 | 0.23 |
| | | 0.1 | 0.30 |
| | | 0.05 | 0.49 |
| 3 | 0.5 | None | 0.24 |
| | | 1 | 0.08 |
| | | 0.5 | 0.12 |
| | | 0.2 | 0.18 |
| 4 | 0.5 | None | 0.39 |
| | | 1 | 0.12 |
| | | 0.5 | 0.15 |
| | | 0.2 | 0.21 |
| 5 | 0.5 | None | 0.68 |
| | | 1 | 0.08 |
| | | 0.5 | 0.19 |
| | | 0.2 | 0.33 |
| 6 | 0.5 | None | 0.51 |
| | | 0.5 | 0.33 |
| 7 | 0.5 | None | 0.20 |
| | | 0.5 | 0.06 |
| | | 0.1 | 0.12 |
| 8 | 0.5 | None | 0.48 |
| | | 0.5 | 0.21 |
| | | 0.1 | 0.39 |
| 9 | 0.5 | None | 0.22 |
| | | 0.5 | 0.06 |
| 10 | 0.5 | None | 0.38 |
| | | 0.5 | 0.11 |
| 11 | 0.5 | None | 0.77 |
| | | 0.5 | 0.53 |
| 12 | 0.5 | None | 0.55 |
| | | 0.5 | 0.41 |

The effect (T/C) achieved by the oral administration of 1 m. mol/kg of uracil (b) alone is 0.96.

Tables 1 and 2 reveal the following. When the 5-fluorouracil (a) is used conjointly with uracil (b), the 5-fluorouracil concentration remains almost at the same level in the blood but greatly increases in the cancer tissues and that the use of uracil (b) with any 5-fluorouracil (a) gives an increased anti-cancer effect. These results show that 5-fluorouracils (a), if convertible to 5-fluorouracil in the living body and when used in combination with uracil (b), afford high anti-cancer effects synergically enhanced by the conjoint use of uracil (b) when the cancer is a cancer sensitive to 5-fluorouracil.

(3) Typical examples of 5-fluorouracils (a) are orally given to rats at a dose of 1 m. mol/kg. The concentration of 5-fluorouracil in the blood is measured 2, 4 and 8 hours after the administration. The results are listed in Table 3, which reveals that Compounds 13 to 29 are all converted to 5-fluorouracil in the living body. Thus these compounds produce increased effects when used conjointly with uracil (b).

TABLE 3

| 5-Fluorouracil (a) (Compd. No.) | Concentration of 5-fluorouracil in blood (μg/ml) | | |
|---|---|---|---|
| | 2 hr | 4 hr | 8 hr |
| 13 | 0.03 | 0.06 | — |
| 14 | 0.03 | 0.02 | — |
| 15 | 0.07 | — | — |
| 16 | 0.14 | — | — |
| 17 | 4.7 | 0.11 | — |
| 18 | 0.11 | 0.11 | 0.16 |
| 19 | 0.02 | — | — |
| 20 | 0.02 | 0.02 | — |
| 21 | 0.19 | 0.27 | 0.26 |
| 22 | 0.17 | 0.25 | 0.14 |
| 23 | 0.28 | 0.38 | 0.24 |
| 24 | 0.02 | 0.02 | 0.03 |
| 25 | 0.02 | 0.05 | 0.04 |
| 26 | 0.06 | 0.24 | 0.05 |
| 27 | 0.26 | 0.35 | 0.27 |
| 28 | 6.6 | 0.78 | 0.35 |
| 29 | — | 0.02 | — |
| 30 | 0.01 | 0.01 | 0.01 |
| 31 | 0.01 | 0.01 | 0.01 |
| 32 | 3.8 | 0.12 | 0.02 |
| 33 | 0.11 | 0.01 | 0.01 |
| 34 | 0.38 | 0.95 | 0.26 |
| 35 | 0.11 | 0.14 | 0.08 |
| 36 | 0.17 | 0.43 | 0.28 |
| 37 | 0.03 | 0.04 | 0.03 |
| 38 | 0.03 | 0.02 | 0.01 |
| 39 | 0.08 | 0.09 | 0.07 |
| 40 | 13.7 | 7.9 | 8.6 |
| 41 | 1.57 | 0.21 | 0.06 |
| 42 | 0.03 | 0.03 | 0.08 |
| 43 | 0.05 | 0.02 | 0.03 |

(4) Compositions formulated according to Preparations 1 to 8 given above are tested by the foregoing method for effects on AH-130. Table 4 shows the results.

TABLE 4

| Prepn. No. | Method of administration | Components and dosage (mg/kg) | | Anti-cancer effect (T/C) | Anti-cancer effect* (control) (T/C) |
|---|---|---|---|---|---|
| 1 | Oral | Compd. 2 | 100 | 0.39 | 0.68 |
| | | Uracil | 20 | | |
| 2 | " | Compd. 3 | 120 | 0.16 | 0.25 |
| | | Uracil | 60 | | |
| 3 | " | Compd. 4 | 50 | 0.28 | 0.45 |
| | | Uracil | 25 | | |
| 4 | " | Compd. 3 | 120 | 0.11 | 0.25 |
| | | Uracil | 120 | | |
| 5 | " | Compd. 5 | 100 | 0.41 | 0.72 |
| | | Uracil | 25 | | |
| 6 | I.v. | Compd. 1 | 10 | 0.30 | 0.66 |

TABLE 4-continued

| Prepn. No. | Method of administration | Components and dosage (mg/kg) | | Anti-cancer effect (T/C) | Anti-cancer effect* (control) (T/C) |
|---|---|---|---|---|---|
| 7 | " | Uracil<br>Compd. 2<br>Uracil | 2<br>100<br>10 | 0.53 | 0.61 |
| 8 | Via anus | Compd. 2<br>Uracil | 100<br>20 | 0.38 | 0.51 |

*Determined with use of compositions formulated in the same manner as above except that no uracil (b) is used.

(5) The anti-cancer compositions of this invention are tested in mice by the following methods to determine acute toxicity, therapeutic effect and theapeutic index.

(a) Acute toxicity

Male mice of ICR strain weighing 22±1 g are used, 5 mice in each group. A 5-fluorouracil (a) and uracil (b) in the proportions listed in Table 5 are suspended in a 5% solution of gum arabic to prepare a suspension, which is forcibly orally administered to each mouse through a tube at a dose of 1 ml/100 g. Over the following period of three weeks the mice are checked every day for poisoning, body weight and mortality. The $LD_{50}$ is determined according to the up-and-down method 3 weeks after the administration. The results are given in Table 5.

(b) Therapeutic effect

Tissues of sarcoma 180, $2 \times 10^6$, are subcutaneously transplanted in the back of male mice of ICR strain (6 mice in each group). A 5-fluorouracil (a) and uracil (b) in the proportions listed in Table 5 are suspended in a 5% solution of gum arabic to prepare a suspension. Twenty-four hours after the transplantation and during the following seven consecutive days the suspension is orally given to the animal once every day. On the 10th day after the transplantation, the tumor is removed from the body and weighed to calculate the average weight (T) of the tumors in the group to which the composition has been given and the corresponding weight (C) in the control group to determine the ratio T/C. The effective dose ($ED_{50}$) for achieving 50% cancer inhibition is determined from the dose-response curve involving the dose and effect (T/C). The results are given in Table 5.

(c) Therapeutic index

The $LD_{50}$ and $ED_{50}$ values obtained above are used to determine the therapeutic index ($LD_{50}/ED_{50}$). The results are also listed in Table 5.

TABLE 5

| 5-Fluorouracil (a) (Compd. No.) | (b)/(a) mol ratio[1] | $LD_{50}$[2] (mg/kg) | $ED_{50}$[2] (mg/kg) | Therapeutic index ($LD_{50}/ED_{50}$) |
|---|---|---|---|---|
| 1 | 0 | 115 | 18.5 | 6.2 |
| | 2.5 | 115 | 8.5 | 13.5 |
| | 10 | 97 | 6.0 | 16.2 |
| 2 | 0 | 820 | 140 | 5.9 |
| | 2.5 | 446 | 20 | 22.3 |
| | 10 | 265 | 11 | 24.1 |
| 3 | 0 | 2224 | 118 | 18.8 |
| | 2.5 | 1894 | 63 | 30.1 |
| | 10 | 1158 | 27 | 42.9 |
| 4 | 0 | 1260 | 60 | 21.0 |
| | 2.5 | 980 | 24 | 40.8 |
| | 10 | 644 | 20 | 32.2 |
| 5 | 0 | 1000 | 112 | 8.9 |
| | 2.5 | 446 | 26 | 17.2 |
| | 10 | 191 | 13 | 14.5 |
| 6 | 0 | 945 | 132 | 7.2 |
| | 2.5 | 945 | 78 | 12.1 |
| | 10 | 693 | 41 | 16.9 |
| 7 | 0 | 1021 | 78 | 13.1 |
| | 2.5 | 687 | 29 | 23.7 |
| | 10 | 381 | 16 | 23.8 |
| 8 | 0 | 1167 | 234 | 5.0 |
| | 2.5 | 973 | 88 | 11.1 |
| | 10 | 427 | 48 | 8.9 |
| 9 | 0 | 332 | 101 | 3.3 |
| | 2.5 | 269 | 39 | 6.9 |
| | 10 | 179 | 28 | 6.4 |
| 10 | 0 | 320 | 111 | 2.9 |
| | 2.5 | 222 | 37 | 6.0 |
| | 10 | 157 | 28 | 5.6 |
| 11 | 0 | 867 | 186 | 4.7 |
| | 2.5 | 723 | 88 | 8.2 |
| | 10 | 358 | 49 | 7.3 |
| 12 | 0 | >5000[3] | 362 | — |
| | 2.5 | >2903[3] | 224 | — |
| | 10 | >1084[3] | 163 | — |

[1]The mole ratio of uracil (b) to 5-fluorouracil (a).
[2]Expressed in terms of the amount (mg/kg) of 5-fluorouracil (a).
[3]Maximum amount that can be physiologically administered.

What is claimed is:

1. An anti-cancer composition for delivering 5-fluorouracil to cancer tissues, of a cancer sensitive to 5-fluorouracil, in warm-blooded animals, said composition comprising a pharmaceutically effective amount of 1-(n-hexylcarbamoyl)-5-fluorouracil and an effective amount of uracil wherein about 0.1 to about 10 moles of uracil are used per mole of 1-(n-hexylcarbamoyl)-5-fluorouracil.

2. An anti-cancer composition as defined in claim 1 wherein about 0.1 to about 5 mols of the uracil is used per mol of the 1-(n-hexylcarbamoyl)-5-fluorouracil.

3. An anti-cancer composition as defined in claim 2 wherein about 0.1 to about 2 mols of the uracil is used per mol of the 1-(n-hexylcarbamoyl)-5-fluorouracil.

4. An anti-cancer composition as defined in claim 1 which is an oral preparation.

5. An anti-cancer composition as defined in claim 1 which is a parenteral solution.

6. An anti-cancer composition as defined in claim 1 which is a suppository.

7. A method of delivering 5-fluorouracil to a cancer sensitive to 5-fluorouracil in a warm-blooded animal, the method comprising administering to the animal the anti-cancer composition of claim 1 in the form of a single preparation in an amount which is effective to deliver an anti-cancer amount of 5-fluorouracil to the cancer.

8. A method of delivering 5-fluorouracil to a cancer sensitive to 5-fluorouracil in a warm-blooded animal, the method comprising administering to the animal at least one 5-fluorouracil (a) and uracil (b) in separate doses, wherein the 5-fluorouracil (a) is 1-(n-hexylcarbamoyl)-5-fluorouracil wherein about 0.1 to about 10 moles of uracil (b) is used per mole of 5-fluorouracil (a), in an amount which is effective to deliver an anti-cancer effective amount of 5-fluorouracil to the cancer.

* * * * *